United States Patent [19]

Kaltenbach

[11] Patent Number: 4,848,342
[45] Date of Patent: Jul. 18, 1989

[54] DILATION CATHETER

[76] Inventor: Martin Kaltenbach, Falltorweg 8, 6072 Dreieich-Buchschlag, Fed. Rep. of Germany

[21] Appl. No.: 905,776

[22] Filed: Sep. 10, 1986

[30] Foreign Application Priority Data

Sep. 13, 1985 [DE] Fed. Rep. of Germany ....... 3532653

[51] Int. Cl.$^4$ ............................................ A61M 29/00
[52] U.S. Cl. ................................... 128/341; 128/343; 604/104
[58] Field of Search ...................... 128/341, 345, 348.1, 128/325, 10, 343, 344; 604/104–109, 104

[56] References Cited

U.S. PATENT DOCUMENTS

| 207,932 | 9/1878 | Alvord | 128/341 |
|---|---|---|---|
| 216,396 | 6/1879 | Guest | 604/104 |
| 2,816,552 | 12/1957 | Hoffman | 128/341 |
| 4,276,874 | 7/1981 | Wolvek et al. | 128/10 |
| 4,425,908 | 1/1984 | Simon | 128/325 |
| 4,494,531 | 1/1985 | Giantarco | 128/325 |
| 4,503,569 | 3/1985 | Dotter | 128/325 |
| 4,553,545 | 11/1985 | Maass et al. | 128/341 |
| 4,649,922 | 3/1987 | Wiktor | 128/344 |
| 4,650,466 | 3/1987 | Luther | 128/343 |
| 4,655,771 | 4/1987 | Wallsten | 128/343 |
| 4,706,671 | 11/1987 | Weinrib | 604/104 |

OTHER PUBLICATIONS

M. Kaltenbach, "The Long Wire Technique—A New Technique for Steerable Balloon Catheter Dilatation of Coronary Artery Stenoses" *European Heart Journal*, (1984) vol. 5, pp. 1004–1009.

C. Vallbracht et al., "Doppel-Langfrahttechnik zur Ballon-Dilatation von Verzgeigungsstenosen" *Herz Kreislauf*, vol. 18, (8/86), pp. 378–382.

Sales Brochure entitled "Softip PTCA Guiding Catheters" copyrighted Angiomedics, 5/86, four pages.

Hansen et al., "Invivo Mechanical Thrombolysis In Subacute Canine Arterial Occlusion" Abstracts of the 58th Scientific Sessions, Nov. 1985, III-469.

*Primary Examiner*—C. Fred Rosenbaum
*Assistant Examiner*—Kathleen Daley
*Attorney, Agent, or Firm*—Hill, Van Santen, Steadman & Simpson

[57] ABSTRACT

A rotatable dilatation catheter comprising a pressure member formed by a coil of wire having open turns adjacent a distal end of the coil with the open turns being expandable to form a pressure member capable of obtaining various diameters. The enlargement of the diameter of the pressure member can occur by means of forming the member of an elastic material which will tend to expand, by means of applying a compressive axial force to the open turns to cause their radially expansion and/or applying a centrifugal force to the turns.

6 Claims, 1 Drawing Sheet

DILATION CATHETER

BACKGROUND OF THE INVENTION

The present invention is directed to a rotating dilatation catheter comprising a pressure member attached to a distal end of the catheter. The pressure member can have variable dimensions and is provided for exerting a pressure against a constricted vessel wall.

A catheter having a pressure member at a distal end is known. An example is a catheter with a balloon formed by a membrane, which balloon is expanded by fluid under pressure of up to about 10 bars which fluid is supplied through the catheter so that the balloon will assume a cylindrical shape having a defined diameter of about 2 through 4 mm when placed in a coronary vessel. A pressure can be exerted on the constricted vessel wall with the balloon so that the constriction can be eliminated in this way. In the unpressurized condition, the membrane will lie close against the catheter and is thus, introduced into the constriction from a guiding catheter in a known manner.

SUMMARY OF THE INVENTION

The object of the present invention is to provide a dilatation catheter that can be easily introduced into a fine or blocked vessel and that has a shape which is optimumly adapted to the respective conditions in the vessel to be treated. It is also an object of the present invention to provide an dilatation catheter which does not require a gas or a fluid agent for the expansion of a balloon and which will not block flow of the blood in the vessel while in an expanded condition.

The objects are achieved by a rotatable dilatation catheter which can have a pressure member attached to a distal end thereof, said pressure member being variable in dimensions and being provided for reopening or expanding constricted blood vessels. The pressure member is composed of a flexible, torsionally stable element helically wound into a coil having open turns adjacent the distal end of the catheter, and means for changing the diameter of the turns of the pressure member.

The catheter is composed of a flexible, torsionally stable element. At its front or distal end, it can carry a pressure member that has turns that are variable in diameter. The rotation occurs manually or from a motor attached to the proximal end of the catheter. The change in diameter of the turns of the pressure member will occur due to its elasticity, due to the centrifugal forces produced by the rotational speed, or by means of an axial compression of the turns. To this end, a wire that allows a change in diameter to be produced by exerting a pull can be provided on the inside of the coil of the catheter.

Other advantages and objects will be apparent from the following description, drawings and claims.

DESCRIPTION OF THE PREFERRED EMBODIMENTS

Figure 1:
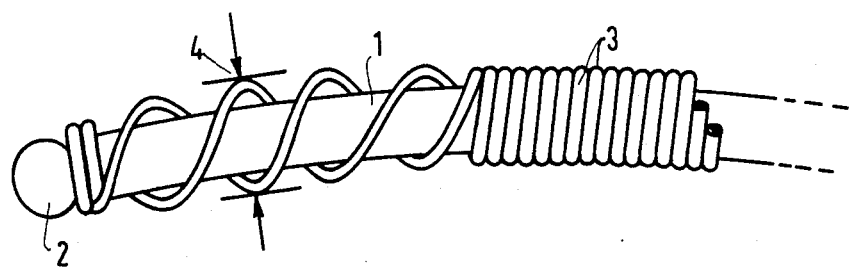
FIG. 1 is a side view of a dilatation catheter in accordance with the present invention.
Figure 2:
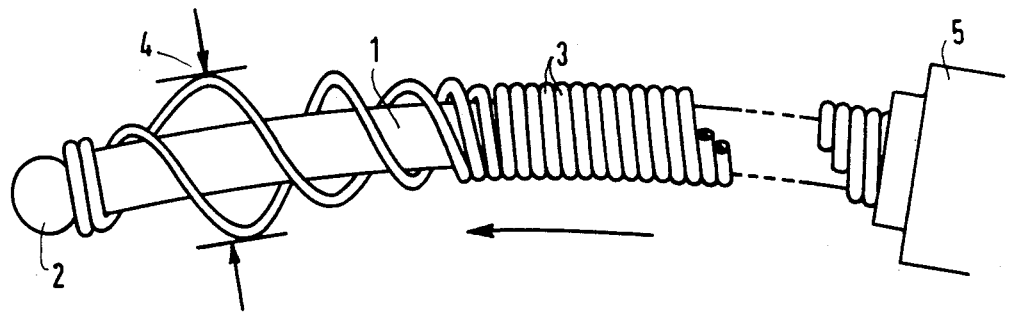
FIG. 2 is a side view of a dilatation catheter of FIG. 1 with dimensions of the catheter increased for the purpose of eliminating a constriction.

The principles of the present invention are particularly useful in a dilatation catheter which is shown and illustrated in FIGS. 1 and 2. The catheter includes a flexible wire or elongated member 1 which is provided with a swelling or head with a spherically curved surface 2 at its distal end. A spring coil 3 is slipped onto the wire 1 and this spring coil has opened turns which are radially expandable at its distal end to form a pressure member 4. In the illustrated embodiment, the coil 3 is a double coarse coil of steel wires, which adjacent a distal end of the wire 1 has an increased spacing between the adjacent turns to form open turns. The diameter of the pressure member can be increased by axially compressing the open turns of the spring coil 3. The axially compression can be produced by a relative movement of the wire 1 in the coil 3 with the head 2 being moved towards the right to engage and to axially compress the open turns of the coil 3 and thus, enlarge the diameter of the pressure member 4 from about 1.8 mm to about 4 mm.

For the treatment of constrictions, the catheter is advanced in the direction of the arrow of FIG. 2 into the constriction of the closed blood vessel. The catheter is placed in rotation by an electrical motor 5 which is secured at the proximal end of the catheter so that easy passage of the distal end becomes possible. In order to eliminate the constriction, a pull is exerted on the wire 1 while continuing rotation of the coil 3 and thus, the pressure member 4 and the diameter of the pressure member 4 will be increased.

The significant advantages of the dilatation catheter of the present invention are as follows:

1. Due to the rotation, a reduction of friction in the axial direction will be present during insertion through a guide catheter and into a vessel;

2. Due to eliminating a balloon sheath, a possibility of passing even extremely narrow stenoses or occlusions due to the small outside diameter and low friction losses of the catheter are present;

3. Due to the method of expanding the catheter, variable expansion possibilities by changing the diameter of the end piece during engagement are present; and 4. Due to the structure of the pressure member, no interruption in the flow of blood during an expanding procedure will occur. For organs, such as hearts, brains and kidneys, that are especially sensitive to an interruption in the blood supply, the inadequate circulation is avoided and an especially gentle, slow expansion of the constriction without a time limit is thus possible.

The expansion of a pressure member can also be achieved employing an elastic material which will assume an expanded position as soon as it leaves the guiding catheter. In a different type of pressure member the expansion can be achieved by changing the speed of rotation so that an increase centrifugal force will be applied to cause the open turns of the pressure member to move radially outward. A third possibility is to pull a wire, such as the wire 1, that extends through the coil, to cause an axial compression force on the coil member to cause expansion. It is also possible to use combinations of the rotation and/or changing the axial stress on the coil to cause the expansion. It is conceivable that a pull on the wire 1 can be completely eliminated by means of appropriate selection of the rotation speed.

Although various minor modifications may be suggested by those versed in the art, it should be understood that I wish to employ within the scope of the patent granted hereon, all such modifications as reasonably and properly come within the scope of my contribution to the art.

I claim:

1. A rotatable dilation catheter comprising a pressure member attached to a distal end of the catheter, said pressure member being variable in dimensions and being provided for reopening and expanding constricted blood vessels, said pressure member being a flexible, torsionally stable element helically wound into a coil having open turns adjacent the distal end of the catheter to form said pressure member, means comprising an electric motor for rotating said catheter as it is being introduced into an area of constriction in a blood vessel, and means for changing the diameter of the open turns of the pressure member by applying mechanical forces to said turns of the coil by increasing the rotational speed to increase the centrifugal forces being applied to the open turns of said coil.

2. A rotatable dilatation catheter according to claim 1, wherein the coil forming the pressure member surrounds a wire, the distal end of said coil being engaged by the distal end of said wire, said means for changing the diameter further includes relatively moving the wire to the coil to provide an axial compressive force on the coil to cause the open turns to be radially expanded.

3. A rotatable dilatation catheter comprising a pressure member attached to a distal end of the catheter, said pressure member being variable in dimensions and being provided for reopening and expanding constricted blood vessels, said pressure member being a flexible, torsionally stable element helically wound into a coil having open turns adjacent the distal end of the catheter to form said pressure member; a wire extending axially through the coil having a distal end engaging the distal end of the coil; means for rotating said catheter as it is being introduced into an area of constriction in a blood vessel, said means for rotating said catheter comprising an electrical motor being connected to a proximal end of the catheter; and means for changing the diameter of the open turns of the pressure member by applying mechanical forces to said turns of the coil, said means for changing the diameter comprises relatively moving the wire and the coil axially to each other to apply an axial compressive force on the open turns of said coil, and increasing the speed of rotation of said catheter to increase the centrifugal forces as an axial displacement between the wire and coil occurs.

4. A rotatable dilatation catheter comprising an elongated member having a distal end and a proximal end; means engaging the proximal end of the member for rotating said member as the distal end of the member is moved through a constriction in a blood vessel, said means for rotating being an electrical motor connected to the proximal end of the elongated member of the catheter; a pressure member being attached to the distal end of the elongated member, said pressure being variable in dimensions and being provided for reopening and expanding constricted blood vessels, said pressure member being a flexible torsionally stable element helically wound into a coil having open turns adjacent the distal end of an elongated member to form said pressure member; and means for changing the diameter of the open turns of the pressure member by applying a mechanical force to said turns by increasing the speed of rotation of the catheter by said electric motor to increase the centrafugal forces being applied to the open turns of the coil forming the pressure member.

5. A rotatable dilatation catheter comprising an elongated member having a distal end and a proximal end and means for continuously rotating said member as the distal end of the member is introduced into an area of a constriction in a blood vessel, said means for continuously rotating comprising an electrical motor being connected to the proximal end of the elongated member of the catheter so that the continuous rotation of the member reduces friction as the catheter advances through the vessel and the distal end penetrates the constriction.

6. A rotatable dilatation catheter according to claim 5, wherein said distal end is a head with a spherically curved surface.

* * * * *